(12) United States Patent
Shang et al.

(10) Patent No.: US 9,051,524 B2
(45) Date of Patent: Jun. 9, 2015

(54) METHOD FOR REFINING POLYOXYMETHYLENE DIALKYL ETHERS BY CATALYTIC HYDROGENATION USING A FIXED BED

(71) Applicant: Dongfang Hongsheng New Energy Application Technology Research Institute Co., Ltd., Beijing (CN)

(72) Inventors: Hongyan Shang, Beijing (CN); Zhengpeng Hong, Beijing (CN); Yu Han, Beijing (CN)

(73) Assignee: DONGFANG HONGSHENG NEW ENERGY APPLICATION TECHNOLOGY RESEARCH INSTITUTE CO., LTD., Beijing (CN)

( * ) Notice: Subject to any disclaimer, the term of this patent is extended or adjusted under 35 U.S.C. 154(b) by 0 days.

(21) Appl. No.: 14/257,712

(22) Filed: Apr. 21, 2014

(65) Prior Publication Data

US 2014/0364653 A1    Dec. 11, 2014

(30) Foreign Application Priority Data

Jun. 9, 2013    (CN) .......................... 2013 1 0231273

(51) Int. Cl.
    *C10L 1/02*      (2006.01)
    *C08G 2/12*      (2006.01)
    *C07C 41/58*      (2006.01)

(52) U.S. Cl.
    CPC . *C10L 1/02* (2013.01); *C07C 41/58* (2013.01); *C08G 2/12* (2013.01)

(58) Field of Classification Search
    USPC ......................................................... 568/699
    See application file for complete search history.

(56) References Cited

U.S. PATENT DOCUMENTS

| | | | |
|---|---|---|---|
| 2,276,192 A | 3/1942 | Hanford et al. | |
| 2,449,469 A | 9/1948 | Gresham et al. | |
| 3,816,478 A * | 6/1974 | Washall et al. | 549/542 |
| 4,153,578 A | 5/1979 | De Thomas et al. | |
| 6,166,266 A | 12/2000 | Hagen et al. | |
| 6,265,528 B1 | 7/2001 | Hagen et al. | |
| 6,437,195 B2 | 8/2002 | Hagen et al. | |
| 2007/0260094 A1 | 11/2007 | Schelling et al. | |
| 2008/0207954 A1 | 8/2008 | Stroefer et al. | |
| 2014/0364652 A1 * | 12/2014 | Hong et al. | 568/621 |

FOREIGN PATENT DOCUMENTS

| | | |
|---|---|---|
| CN | 102173984 A | 9/2011 |
| CN | 102180778 A | 9/2011 |
| EP | 1 070 755 A1 | 1/2001 |

OTHER PUBLICATIONS

Database CAPLUS on STN, Acc. No. 1983:576871, Pavlikov et al., SU 1024458 A1 (Jun. 23, 1983) (abstract).*

* cited by examiner

*Primary Examiner* — Brian J Davis
(74) *Attorney, Agent, or Firm* — Birch, Stewart, Kolasch & Birch, LLP (57) ABSTRACT

The present invention relates to a method for refining polyoxymethylene dialkyl ethers by catalytic hydrogenation using a fixed bed, wherein, using a fixed bed reactor for refining by hydrogenation, an equilibrium system containing polyoxymethylene dialkyl ethers products is refined by catalytic hydrogenation, so as to remove formaldehyde contained therein. The refining method by hydrogenation described in the present invention can remarkably increase the separation and purification efficiency of polyoxymethylene dialkyl ether products with various polymerization degree, and the polyoxymethylene dialkyl ethers obtained after subsequent rectification have a purity greater than 99.5%, a product yield greater than 97% and an atom utilization ratio close to 100%.

14 Claims, 1 Drawing Sheet

METHOD FOR REFINING POLYOXYMETHYLENE DIALKYL ETHERS BY CATALYTIC HYDROGENATION USING A FIXED BED

TECHNICAL FIELD

The present invention relates to a method for refining polyoxymethylene dialkyl ethers by catalytic hydrogenation using a fixed bed, which belongs to the field of coal-based energy chemical industry, clean energy and refining by chemical process.

BACKGROUND OF THE INVENTION

Recent investigation shows that, the apparent consumption of diesel fuel in China has already mounted up to about 167 million tons, which leads to frequent occurrence of short supply of diesel fuel (the domestic demand ratio of diesel fuel to petrol is about 2.5:1, but the production ratio thereof is about 2.3:1). Besides the reasons of unreasonable pricing of different types of oil products, and slow price linkage mechanism of domestic petroleum products with international crude oil, the fundamental reason is the constrains of resource shortage. Traditionally, diesel fuel is made from petroleum feedstock, and the resource endowment of China characterized in relatively "rich in coal, poor in oil, and lack in gas" leads to increasingly prominent contradiction between petroleum supply and relatively fast sustainable development of economics and society. Since China became a net importer of petroleum in 1993, the import volume increases fast and constantly, and the foreign-trade dependence already surpassed 56% after 2011, which has a severe impact on national strategic security of energy.

Furthermore, the worsening of crude oil quality leads to continuous scale expansion of domestic catalytic processing of heavy oil and increasing percentage of diesel fuel produced by catalytic processing, which results in gradual decrease of the cetane number (CN value) of diesel fuel products and significant increase of noxious substance discharged after combustion, therefore, the urgent problem to be solved is to increase the CN value of diesel fuel.

The tail gas discharged by a diesel engine contains a large amount of noxious substance such as unburned hydrocarbon compounds and particulate matter (PM), as well as CO, $CO_2$ and $NO_x$, which is one of the main sources of PM2.5 contamination in urban air. International Agency for Research on Cancer (IARC) affiliated to World Health Organization (WHO) declared in June, 2012 the decision to elevate the cancer hazard ranking of diesel engine tail gas, from "possibly carcinogenic" classified in 1988 to "definitely carcinogenic". As scientific research advances, now there is enough evidence to prove that diesel engine tail gas is one of the reasons that cause people to suffer from lung cancer. Furthermore, there is also limited evidence indicating that, inhaling diesel engine tail gas is relevant to suffering from bladder cancer. People come into contact with diesel engine tail gas through various channels in daily life and work. IARC hopes that this reclassification can provide reference for national governments and other decision makers, so as to actuate them to establish more strict discharge standards of diesel engine tail gas. This significant decision undoubtedly puts forward harsher requirements of diesel fuel quality.

Reducing the content of noxious substance such as sulfur, nitrogen and aromatic hydrocarbon in fuels by petroleum refining process such as hydrogenation is an effective technical route to improve fuel quality, but has very demanding requirements of hydrogenation catalyst and reaction process, with relatively high processing cost. Internationally, many scientific research institutes are carrying out research and development on production technologies of oxygen-containing blending components for petrol and diesel fuel, especially those diesel fuel blending components with high oxygen content and high cetane number, and this has recently become a research hotspot in the technical field of new energy.

Research has indicated that, in consideration of inherent characteristics of oxygen-containing fuel, when oxygen-containing coal-based or methanol-based substance with a high cetane number is added into the fuel as a fuel additive, the discharge of hydrocarbon and CO, especially soot, can be effectively reduced, without changing the original parameters of the engine or increasing the discharge of $NO_x$.

So far, a plenty of researches indicate that, polyoxymethylene dimethyl ethers (abbreviated as PODEn or $POMDME_n$, n=2-8), which has a general formula of $CH_3(OCH_2)_nOCH_3$ and is a yellow liquid with a high boiling point, an average cetane number reaching above 63 and increasing dramatically as its polymerization degree increases, an average oxygen content of 47%-50%, a flash point of about 65.5° C., and a boiling point of 160-280° C., is a type of clean diesel fuel blending component with a high cetane number, and also is a world-recognized environmental friendly fuel component. Polyoxymethylene dimethyl ethers can be blended into diesel fuel, and can significantly improve the performance of diesel fuel, without the need to modify the engine oil feeding system of the in-use vehicle. However, it is discovered in practical usage that, the cetane number of polyoxymethylene dimethyl ethers is largely influenced by its polymerization degree, and polyoxymethylene dimethyl ethers with a relatively high polymerization degree is required for achieving a better effectiveness. But, in consideration of the inherent difficulty of polymerization reaction, relatively demanding requirements are put forward not only for equipment but also for process conditions, with increased difficulty of processing, separating and purifying. Therefore, people gradually move their focus onto characteristic of polyoxymethylene dialkyl ethers. Polyoxymethylene dialkyl ethers are a series of acetal polymers with low relative molecular weights, which comprise oxymethylene groups as main chain and low carbon alkyl groups as terminal groups, with a general formula of $R(OCH_2)_nOR$ where R is an alkyl chain of $C_nH_{2n+1}$.

Since the terminal groups of polyoxymethylene dialkyl ethers has relatively high molecular weights in its own, only relatively low polymerization degree is required to achieve a cetane number performance similar to that of polyoxymethylene dimethyl ethers, and the difficulty during the preparation process is relatively low. Polyoxymethylene dialkyl ethers have good environmental protection performance, and when blended into diesel fuel at a certain percentage, they can increase oxygen content of the oil product, and greatly reduce the discharge of contaminants such as $SO_x$, unburned hydrocarbon compounds, PM particulate black smoke and CO from vehicle tail gas. Because polyoxymethylene dialkyl ethers have a high cetane number and physical property similar to that of diesel fuel, they are also a type of diesel fuel additive with very high application value.

Synthesis of polyoxymethylene dialkyl ethers (including polyoxymethylene dimethyl ethers) may be carried out by processing synthesis gas through a series of steps of methanol, formaldehyde, methylal, polyformaldehyde and dimethyl ether etc. China is a famous huge country of coal storage, and Chinese technologies of producing methanol from coal, producing methanol from natural gas and producing methanol from coke-oven gas are increasingly mature, and the production capacity of methanol broke through 50 million tons in 2012, but the equipment operation rate is merely about 50%, thus the problem of methanol surplus has already become very prominent, and the industrial chain of coal chemical industry is in an urgent need to be further extended. Therefore, developing the technology of producing polyoxymethylene dialkyl ethers from coal-based methanol can not only provide a new technology to significantly increase diesel fuel product quality, but also improve the feedstock structure of diesel fuel production, so as to make it more suitable for the resource endowment of domestic fossil energy and enhance the strategic security of domestic supply of liquid fuel for engines.

The preparation process of polyoxymethylene dialkyl ethers should comprise three major process units, wherein, the first unit is a synthesis unit where cascade polymerization reactions and thermodynamic equilibrium reactions catalyzed by acidic catalysts take place; the second unit is a pretreatment unit where processing steps such as deacidifying by neutralization and dehydration by drying take place; and the third unit is a unit for rectification and separation of the downstream products, and this unit attempts to separate polyoxymethylene dialkyl ethers by simple rectification or complicated rectification such as extractive rectification, azeotropic rectification, etc.

So far, domestic and foreign researches on preparation process of polyoxymethylene dialkyl ethers (including polyoxymethylene dimethyl ethers) mainly focus on the aspects of feedstock selection, condition optimization and catalyst system optimization of the synthesis unit, as well as the process technology to improve the distribution of target products and increase product yield. As for optimization of synthesis feedstocks, there are mainly the following five techniques: the first technique is synthesizing polyoxymethylene dimethyl ethers from methanol, formaldehyde, aqueous formaldehyde solution or paraformaldehyde feedstocks, with details described in Patent Applications such as U.S. Pat. No. 6,437,195B2, US2008/0207954A1 and EP1070755A1; the second technique is synthesizing polyoxymethylene dimethyl ethers from methylal, trioxane or paraformaldehyde feedstock, with details described in Patent Applications such as US2007/0260094A1 and US2449469A; the third technique is synthesizing polyoxymethylene dimethyl ethers from methanol and dimethyl ether feedstocks, with details described in Patent Application such as U.S. Pat. No. 6,265,528B1; the fourth technique is developed on the basis of the foregoing three techniques, and this technique uses alcohol-containing by-products of other chemical processes in the prior art to synthesize mixture of polyoxymethylene dialkyl ethers with various polymerization degree and various terminal groups, and the major representative techniques are synthesis of polyoxymethylene dialkyl ethers with various polymerization degree and various terminal groups from the feedstock of industrial alcohol brewing by-products or Fischer-Tropsch synthesis by-products or C4, C5 fractions of petroleum, which are disclosed in Chinese Patent Applications CN102173984A and CN102180778A.

In the above-mentioned technical solutions of synthesis of polyoxymethylene dialkyl ethers, the separation and purification of synthesized products is carried out without exception by conventional ordinary rectification, extractive rectification or azeotropic rectification of the prior art, and no further in-depth research is done in respect of the separation and purification unit of target products. However, it is discovered in practical research that, when separating and purifying target products by using the foregoing conventional seemingly viable means, it always leads to that the separation and purification efficiency of products is not high, and the purity of the separated products is not satisfactory, which is not enough to meet the technical standard for blending with fossil diesel fuel and requires subsequent additional purification operations to meet the needs, and no matter how the parameters and conditions of the entire operating process of the separation and purification unit are optimized, the difficult problem about separation and purification efficiency always cannot be solved, and no significant increase in separation and purification efficiency or product purity can be achieved. In practical production, in consideration of economical and various other aspects, no matter how great the efficiency of the synthesis unit at the front is, the incapability of obtaining required products by effective separating and purifying means is always a difficult problem and bottleneck that restrains the development of this technology, which is an urgent matter to be solved in this field.

SUMMARY OF THE INVENTION

The technical problem to be solved in the present invention is, by in-depth research on the process of the unit for separating and purifying polyoxymethylene dialkyl ethers in prior art, to find out the influence reasons for poor separation and purification efficiency of the separation and purification unit and poor purity of the separated products, so as to provide a method for refining polyoxymethylene dialkyl ethers by catalytic hydrogenation using a fixed bed, which is able to significantly increase the separation and purification efficiency and the product purity.

To solve the above-mentioned technical problem, the present invention is achieved by the following technical solutions:

A method for refining polyoxymethylene dialkyl ethers by catalytic hydrogenation using a fixed bed is provided, wherein, using a fixed bed reactor of refining by hydrogenation and in the presence of catalyst, an equilibrium system containing polyoxymethylene dialkyl ethers products is refined by catalytic hydrogenation, so as to remove formaldehyde contained therein, and subsequent separating and purifying operations are performed on the products after formaldehyde removal.

Preferably, the catalyst is a supported Ni-based catalyst system, or an unsupported Cu-based catalyst system.

Specifically, the supported Ni-based catalyst system is a $Ni/Al_2O_3$ supported catalyst modified by K, Mg or Zn, wherein, calculated on the total mass of the catalyst, the loading amount of active ingredient Ni is 5-25 wt %, and the loading amount of K, Mg or Zn is 0.5-5 wt %.

In the supported Ni-based catalyst system, preferably, the loading amount of active ingredient Ni is 10-20 wt %, and the loading amount of K, Mg or Zn is 1-3 wt %.

Specifically, the supported Ni-based catalyst system is $ZrO_2$, $SiO_2$ or activated carbon supported Ni catalyst, wherein, calculated on the total mass of the catalyst, the loading amount of active ingredient Ni is 15-20 wt %.

In said supported Ni-based catalyst system, preferably, the loading amount of active ingredient Ni is 18-20 wt %.

Specifically, the unsupported Cu-based catalyst system is an unsupported Cu—Zn—Al catalyst with active ingredients of CuO, ZnO and $Al_2O_3$, wherein, calculated on the total mass of the catalyst, the content of active ingredient CuO is 25-60 wt %, the content of active ingredient ZnO is 20-50 wt %, and the content of $Al_2O_3$ is 5-25 wt %.

Specifically, the unsupported Cu-based catalyst system is an unsupported Cu—Cr—Al catalyst, wherein, calculated on the total mass of the catalyst, the content of active ingredient CuO is 30-60 wt %, the content of active ingredient $Cr_2O_3$ is 10-45 wt %, and the content of $Al_2O_3$ is 10-30 wt %.

Preferably, the amount of formaldehyde contained in the equilibrium system containing polyoxymethylene dialkyl ethers products is 0.5-20 wt %.

Specifically, the refining by catalytic hydrogenation is carried out at a hydrogen pressure of 1-10 Mpa, a catalytic hydrogenation reaction temperature of 80-160° C., a liquid space velocity of 0.5-4 $h^{-1}$, and a hydrogen-to-oil volume ratio of 100:1-600:1.

Preferably, the refining by catalytic hydrogenation is carried out at a hydrogen pressure of 2-6 Mpa, a catalytic hydrogenation reaction temperature of 100-130° C., a liquid space velocity of 1-2 $h^{-1}$, and a hydrogen-to-oil volume ratio is 200:1-400:1.

Specifically, the separating and purifying operations comprise one or more operations selected from atmospheric distillation, vacuum distillation, flash evaporation, rectification, phase separation and filtration.

The catalyst described in the present invention has very high selectivity, the supported Ni-based catalyst and the unsupported Cu-based catalyst are common products in the prior art, which are commercially available on the market or can be prepared in-house. Wherein, the in-house preparation method can be a solvent method, for instance, 20% NiO-2% ZnO/$Al_2O_3$ catalyst can be prepared by the solvent method with detailed steps as follows: 78 g alumina supporter which has been calcined at 500° C., 77.86 g nickel nitrate hexahydrate crystals and 7.31 g zinc nitrate hexahydrate crystals are successively weighed out, and the nickel nitrate and zinc nitrate crystals that has been weighed out are dissolved in 30 ml water to form a mixed dipping solution; then, by isovolumetric dipping method, the mixed dipping solution are uniformly dropped onto the alumina supporter, and the resulting material is then aired at room temperature, dried at 120° C. for 4 hours, and calcined at 400° C. for 4 hours to produce 20% NiO-2% ZnO/$Al_2O_3$ catalyst. With this method as an example, those skilled in the art can prepare supported catalyst containing any active ingredient based on practical needs.

The aforementioned technical solutions of the present invention have the following advantages, as compared to the prior art:

(1) By in-depth research on the synthesis process of polyoxymethylene dialkyl ethers, the applicant has discovered that, no matter which of formaldehyde, paraformaldehyde or methylal is used as feedstock for the reaction, the entire reaction system is equilibrium and reversible, thus the problem of incomplete reaction with low carbon alcohol (or methanol) always exists, therefore, regardless of how the reaction conditions are improved, there is always 3.5 wt % of formaldehyde (or monomer of depolymerized paraformaldehyde or methylal) unable to completely react in the product system, and the reason that leads to the difficulty of separation and purification of polyoxymethylene dialkyl ether products and the low product purity is mainly that the formaldehyde in the system gives rise to unexpected negative effect, that is, complexation reaction happens between formaldehyde and polyoxymethylene dialkyl ethers with various polymerization degree, resulting in the formation of complicated binary or ternary azeotropic system, so that the products with various polymerization degree are chained together by formaldehyde to form enormous complexation system, which causes it unable to separate, purify or refine the products with various polymerization degree and various terminal groups from the entire product system by ordinary processes such as distillation, not only bringing about great difficulty of separation process, but also severely affecting product yield and economic efficiency; furthermore, in the rectification process oxidization and dismutation of formaldehyde into formic acid takes place to form an acidic environment, and formic acid is a catalyst for reverse decomposition of polyoxymethylene dialkyl ethers, which causes the technical problem that the target products of polyoxymethylene dialkyl ethers are decomposed reversely and new formaldehyde is released in the rectification process; therefore, before separating and purifying the target products, it is necessary to specifically eliminate the small amount of formaldehyde contained in the equilibrium system, in order to release the respective products required and to obtain satisfactory products by other feasible means;

(2) At the same time of research on factors that influence the separation and purification efficiency, it is surprisingly discovered by the applicant that, in the entire equilibrium system after synthesis of products, the water content has a great influence on separation and purification efficiency and purity of the products, therefore, when choosing the process for refining to eliminate formaldehyde, it is necessary to carefully select a reasonable method in order to maximally ensure the separation and purification efficiency and purity of the products;

(3) In the separation and purification process described in the present invention, after careful research, the applicant has inventively discovered the key factors that influence the separation and purification efficiency of polyoxymethylene dialkyl ethers in the prior art, and has achieved high-efficiency and high-purity separation and purification of polyoxymethylene dialkyl ethers with various polymerization degree by specific modification of the above-mentioned factors which have not been cared or considered by those skilled in the art;

(4) In the method of the present invention for refining polyoxymethylene dialkyl ethers by catalytic hydrogenation using a fixed bed, the unreacted formaldehyde contained in the equilibrium system containing polyoxymethylene dialkyl ethers products is transformed into methanol by reduction reaction, so as to break the complicated azeotropic system between formaldehyde and methanol, as well as between formaldehyde and the products, so that polyoxymethylene dialkyl ethers with a purity greater than 99.5% can be produced by atmospheric rectification and/or vacuum rectification of the products, and the product yield of polyoxymethylene dialkyl ethers is greater than 97%, the atom utilization ratio is close to 100%. The technological process has no discharge of waste water or waste residue, thus is an innovative green process and technology to separate and refine polyoxymethylene dialkyl ethers;

(5) The method of the present invention for refining polyoxymethylene dialkyl ethers by catalytic hydrogenation using a fixed bed utilizes a fixed bed reactor for refining by hydrogenation together with a supported Ni-based catalyst system or an unsupported Cu-based catalyst system to specifically and high selectively refine the equilibrium products by hydrogenation of formaldehyde, so as to specifically separate and purify the products with various polymerization degree, and the aforementioned selected catalyst has high activity and high efficiency;

(6) As for the equilibrium system after processing by the refining method of the present invention, subsequent separating operations may be performed by ordinary processing means such as atmospheric rectification and vacuum rectification, and the products with various polymerization degree that have been separated have high purity and high product yield.

BRIEF DESCRIPTION OF THE DRAWINGS

In order to make the present invention more easily and clearly understood, detailed description is further presented below, with reference of accompanying drawings, wherein.

Wherein, the markings in the accompanying drawings are explained as follows: 1-fixed bed synthesis reactor, 2-buffer tank, 3-drying tower, 4-fixed bed reactor of refining by hydrogenation, 5-buffer tank, 6-atmospheric rectification tower, 7-vacuum rectification tower.

DETAILED DESCRIPTION OF EMBODIMENTS

Figure 1:
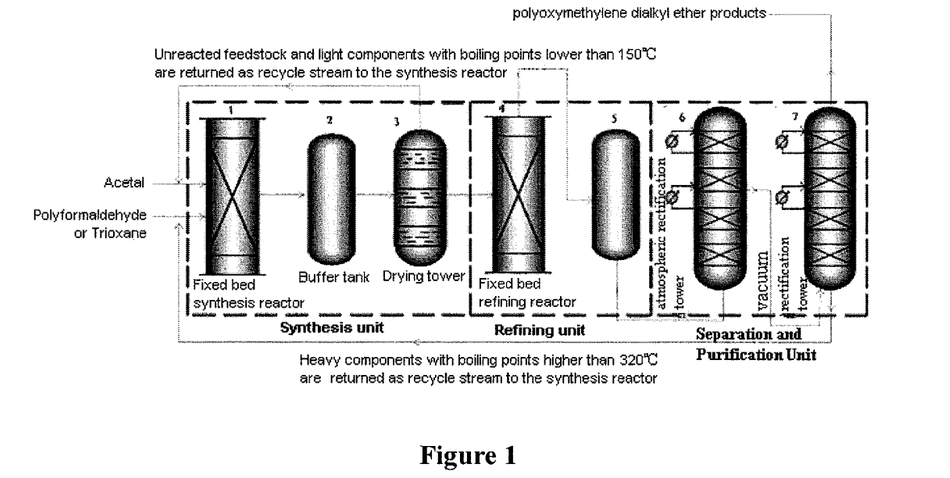
FIG. 1 is a process flow diagram showing the method of producing polyoxymethylene dialkyl ethers described in the present invention.

As shown in FIG. 1, the process of the present invention for preparation of polyoxymethylene dialkyl ethers comprises three major process units, the first unit is a synthesis unit, and its structure comprises a fixed bed synthesis reactor 1, a buffer tank 2, and a drying tower 3, wherein, the equilibrium system obtained by synthesis reaction in the fixed bed synthesis reactor 1 is successively deacidified in the buffer tank 2 and dehydrated in the drying tower 3; the feedstock of synthesis of polyoxymethylene dimethyl ethers mainly consists of two parts: one part is compounds that provide low polyformaldehyde, comprising aqueous formaldehyde solution, trioxane, paraformaldehyde, etc., and the other part is compounds that provide terminal groups, comprising methanol, dimethyl ether, methylal, etc., and the synthesis reaction is a cascade polymerization reaction and a thermodynamic equilibrium reaction catalyzed by acidic catalyst; the second unit is a unit for pretreatment and catalytic refining, and its structure comprises a fixed bed reactor of refining by hydrogenation 4 and a buffer tank 5, wherein, the equilibrium system is successively processed in the fixed bed reactor of refining by hydrogenation 4 and the buffer tank 5, thereby the unreacted formaldehyde is removed; the third unit is a unit for separation and purification by rectification, its structure comprises an atmospheric rectification tower 6 and a vacuum rectification tower 7, wherein, high purity polyoxymethylene dialkyl ethers are finally obtained after the equilibrium system has passed through the atmospheric rectification tower 6 and the vacuum rectification tower 7. The unreacted light components of methylal and methanol as well as the polyoxymethylene dialkyl ethers with boiling points lower than 150° C. are returned as recycle stream to the fixed bed synthesis reactor 1; the heavy components of polyoxymethylene dialkyl ethers with boiling points higher than 320° C. are also returned as recycle stream to the fixed bed synthesis reactor 1.

Figure 2:
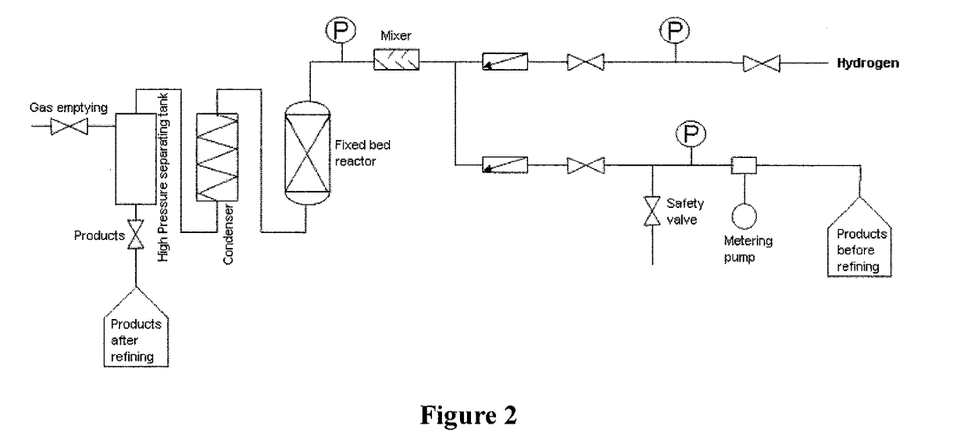
FIG. 2 is a flow diagram of the fixed bed reactor apparatus for refining by hydrogenation described in the present invention.

FIG. 2 illustrates a flow diagram of the fixed bed reactor apparatus of refining by hydrogenation, wherein, the products before refining (the equilibrium system) and hydrogen are mixed at a selected hydrogen-to-oil ratio in a mixer and enter the fixed bed reactor, after being processed by a condenser and a high pressure separating tank, refined products of the equilibrium system are obtained, and subsequent separating and purifying operations are then performed in the separation and purification unit.

In Embodiments 1 to 4 of the present invention, as well as in Comparative Example 1, the equilibrium systems containing polyoxymethylene dimethyl ethers products are the same, the preparation method of which is that:

In a 2 L fixed bed synthesis reactor 1, 60-80 g strongly acidic catalyst of Amberlyst15 cation exchange resin is added, and then 1200 g in total of paraformaldehyde (or trioxane) and acetal (or methanol, ethanol, propanol, butanol, pentanol) at various molar ratios are added, wherein the molar ratios are within 1:1-2:1. Firstly the air in the reactor is replaced by nitrogen, then 1.5 MPa of initial nitrogen is filled in, the reaction mixture is heated up to the reaction temperature of 70-130° C. and reacts under stirring for 0.5-6 hours, thereby the equilibrium system containing polyoxymethylene dimethyl ethers products are obtained, wherein the product distribution and product yield of the target product POMDME$_n$ are shown in Table 1.

TABLE 1 product distribution and yield of the target product POMDME$_n$ of the equilibrium system of products containing polyoxymethylene dimethyl ethers

| Products | Boiling Point/° C. | Content/wt. % |
|---|---|---|
| Formaldehyde | −19.5 | 3.0~10.0 |
| Methanol | 64.7 | 2.0~5.0 |
| Methylal | 42.3 | 28.0~30.0 |
| POMDME$_2$ | 105 | 25.0~26.0 |
| POMDME$_3$ | 156 | 10.0~13.0 |
| POMDME$_4$ | 202 | 5.0~6.0 |
| POMDME$_5$ | 242 | 3.0~3.5 |
| POMDME$_6$ | 280 | 2.0~2.5 |
| POMDME$_7$ | 313 | 0.5~1.0 |
| POMDME$_8$ | 320 | 0.2-0.5 |
| ΣPOMDME$_{2-8}$ wt % | | ~50.0 |

Embodiment 1

Firstly, 20 ml supported Ni-based catalyst system is loaded into a fixed bed reactor of refining by hydrogenation 4, the supported Ni-based catalyst system is a Ni/γ—Al$_2$O$_3$ supported catalyst modified by K, the loading amount of active ingredient Ni is 20 wt %, and the loading amount of K is 3 wt %; firstly, hydrogen is fed in, then the catalyst material is heated up to 400° C. at a temperature increasing rate of 20° C. per hour and then goes through reduction reaction for 8 hours, and the temperature is subsequently reduced to 130° C.

Then, the equilibrium system containing polyoxymethylene dimethyl ethers products is refined by catalytic hydrogenation, and the process conditions are: the hydrogen pressure is 4 Mpa, the bed temperature of the fixed bed is 130° C., the space velocity of liquid is 2 h$^{-1}$, the volume ratio of hydrogen to the products to be hydrogenated (also named as "hydrogen-to-oil" volume ratio) is 400:1, and the products are consecutively refined for 100 hours.

Finally, the formaldehyde contained is hydrogenated into methanol by the catalytic function of the Ni/γ—Al$_2$O$_3$ supported catalyst modified by K, and the methanol generated constitutes a component of the equilibrium products, thereby no other foreign component is generated while removing formaldehyde. The constituents and distribution of the main products before and after refining by catalytic hydrogenation are shown in Table 2.

The equilibrium system after refining by catalytic hydrogenation is separated and purified, and the separation and purification process utilizes the atmospheric rectification technology, with a tower plate number of 10~40, gas temperature of 48~58.0° C. at tower top, temperature of 100~120° C. at tower bottom, feedstock temperature of 60~90° C., and reflux ratio of 1.0~3.0. After the separation and purification is finished, the testing result of separation and purification efficiency of the products is shown in Table 3.

Embodiment 2

Firstly, 20 ml supported Ni-based catalyst system is loaded into a fixed bed reactor of refining by hydrogenation 4, the supported Ni-based catalyst system is Ni/γ—Al$_2$O$_3$ supported catalyst modified by Mg, the loading amount of active ingredient Ni is 15 wt %, and the loading amount of Mg is 2 wt %; firstly, hydrogen is fed in, then the catalyst material is heated up to 450° C. at a temperature increasing rate of 20° C. per hour and then goes through reduction reaction for 8 hours, and the temperature is subsequently reduced to 120° C.

Then, the equilibrium system containing polyoxymethylene dimethyl ethers products is refined by catalytic hydrogenation, and the process conditions are: the hydrogen pressure is 3 Mpa, the bed temperature of the fixed bed is 120° C., the space velocity of liquid is 1 h$^1$, the hydrogen-to-oil ratio is 300:1, and the products are consecutively refined for 120 hours.

Finally, the formaldehyde contained is hydrogenated into methanol by the catalytic function of the Ni/γ—Al$_2$O$_3$ supported catalyst modified by Mg, and the methanol generated constitutes a component of the equilibrium products, thereby no other foreign component is generated while removing formaldehyde. The constituents and distribution of the main products before and after refining by catalytic hydrogenation are shown in Table 2.

This embodiment utilizes the same separation and purification process as in Embodiment 1 to perform the separation and purification operations.

Embodiment 3

Firstly, 20 ml supported Ni-based catalyst system is loaded into a fixed bed reactor of refining by hydrogenation, the supported Ni-based catalyst system is Ni/γ—Al$_2$O$_3$ supported catalyst modified by Zn, the loading amount of active ingredient Ni is 20 wt %, and the loading amount of Zn is 2 wt %; firstly, hydrogen is fed in, then the catalyst material is heated up to 450° C. at a temperature increasing rate of 20° C. per hour and then goes through reduction reaction for 6 hours, and the temperature is subsequently reduced to 100° C.

Then, the equilibrium system containing polyoxymethylene dimethyl ethers products is refined by catalytic hydrogenation, and the process conditions are: the hydrogen pressure is 5 Mpa, the bed temperature of the fixed bed is 100° C., the space velocity of liquid is 1 h$^{-1}$, the hydrogen-to-oil ratio is 300:1, and the products are consecutively refined for 60 hours.

Finally, the formaldehyde contained is hydrogenated into methanol by the catalytic function of the Ni/γ—Al$_2$O$_3$ supported catalyst modified by Zn, and the methanol generated constitutes a component of the equilibrium products, thereby no other foreign component is generated while removing formaldehyde. The constituents and distribution of the main products before and after refining by catalytic hydrogenation are shown in Table 2.

This embodiment utilizes the same separation and purification process as in Embodiment 1 to perform the separation and purification operations.

Embodiment 4

Firstly, 20 ml supported Ni-based catalyst system is loaded into a fixed bed reactor of refining by hydrogenation, the supported Ni-based catalyst system is activated carbon supported Ni catalyst, the loading amount of active ingredient Ni is 18 wt %; firstly, hydrogen is fed in, then the catalyst material is heated up to 350° C. at a temperature increasing rate of 20° C. per hour and then goes through reduction reaction for 8 hours, and the temperature is subsequently reduced to 110° C.

Then, the equilibrium system containing polyoxymethylene dimethyl ethers products is refined by catalytic hydrogenation, and the process conditions are: the hydrogen pressure is 2 Mpa, the bed temperature of the fixed bed is 110° C., the space velocity of liquid is 1 h$^{-1}$, the hydrogen-to-oil ratio is 400:1, and the products are consecutively refined for 80 hours.

Finally, the formaldehyde contained is hydrogenated into methanol by the catalytic function of the activated carbon supported Ni catalyst, and the methanol generated constitutes a component of the equilibrium products, thereby no other foreign component is generated while removing formaldehyde. The constituents and distribution of the main products before and after refining by catalytic hydrogenation are shown in Table 2.

This embodiment utilizes the same separation and purification process as in Embodiment 1 to perform the separation and purification operations.

In Embodiments 1 to 4, the constituents and distribution of the main products before and after catalytic hydrogenation are shown in Table 2 (Note: the symbol "~" therein means being close to).

TABLE 2 constituents and distribution of the main products before and after refining by catalytic hydrogenation

| System | Constituents | | | | | Conversion rate of formaldehyde/% | Selectivity of catalyst/% |
|---|---|---|---|---|---|---|---|
| | Methanol wt % | Formaldehyde wt % | Methylal wt % | ΣPODE$_{2-8}$ wt % | ΣPODE$_{n>8}$ wt % | | |
| Before refining by hydrogenation | 3.7 | 7.8 | 34.0 | 54.0 | 0.5 | — | — |
| After refining by hydrogenation in Embodiment 1 | 11.49 | 0.01 | 34.0 | 54.0 | 0.5 | ~99.8 | ~100 |
| After refining by hydrogenation in Embodiment 2 | 11.47 | 0.03 | 34.5 | 53.5 | 0.5 | ~99.6 | ~100 |
| After refining by hydrogenation in Embodiment 3 | 11.50 | 0.00 | 34.2 | 53.8 | 0.5 | ~100 | ~100 |

TABLE 2-continued constituents and distribution of the main products before
and after refining by catalytic hydrogenation

| System | Constituents | | | | | | |
|---|---|---|---|---|---|---|---|
| | Methanol wt % | Formaldehyde wt % | Methylal wt % | $\Sigma PODE_{2-8}$ wt % | $\Sigma PODE_{n>8}$ wt % | Conversion rate of formaldehyde/% | Selectivity of catalyst/% |
| After refining by hydrogenation in Embodiment 4 | 11.49 | 0.01 | 34.0 | 54.0 | 0.5 | ~99.8 | ~100 |

Thus it can be seen that, the catalyst used in the present invention can effectively solve the problem of eliminating formaldehyde contained in the product system, and meanwhile does not affect other required products in the system, with very high selectivity and efficiency of catalyst.

Comparative Example 1

This comparison example is based on the same equilibrium system containing the polyoxymethylene dimethyl ethers products as in Embodiment 1, but the refining step as in Embodiment 1 is omitted, instead the overall equilibrium system after synthesis directly enters the separation and purification unit, and Comparative Example 1 utilizes the same separation and purification means as in Embodiment 1 to separate and purify the products with various polymerization degree. After the separation and purification is finished, the testing result of separation and purification efficiency of the products is shown in Table 3.

TABLE 3 separation and purification efficency of the products

| Number | Content of $\Sigma PODE_{2-8}$ in the equilibrium products/ wt % | Formaldehyde content after atmospheric rectification/ wt % | Recovery ratio of the target product $\Sigma PODE_{2-8}$/% | Purity of the target product $\Sigma PODE_{2-8}$/% |
|---|---|---|---|---|
| Embodiment 1 | 54.0 | ~0.01 | 99.9 | ~99.7 |
| Comparative example 1 | 54.0 | 8.2 | <32.0 | ~91.8 |

The equilibrium systems containing the polyoxymethylene dialkyl ethers products in Embodiment 5-1 to Embodiment 8-2 of the present invention are the same, the preparation method of which is that:

In a 2 L pressurized fixed bed reactor, 60-80 g strongly acidic catalyst of Amberlyst15 cation exchange resin is added, and then 1200 g in total of paraformaldehyde (or trioxane) and ethanol (or propanol, butanol, pentanol) at various molar ratios are added, wherein the molar ratios are within 1:1-2:1. Firstly, the air in the reactor is replaced by nitrogen, then 1.5 MPa of initial nitrogen is filled in, the reaction mixture is heated up to the reaction temperature of 70~130° C. and reacts under stirring for 0.5~6 hours. Thereby equilibrium systems respectively containing polyoxymethylene diethyl ether products, polyoxymethylene dipropyl ether products, polyoxymethylene dibutyl ether products and polyoxymethylene dipentyl ether products are obtained.

Embodiment 5-1

Firstly, 20 ml supported Ni-based catalyst system is loaded into a fixed bed reactor of refining by hydrogenation, the supported Ni-based catalyst system is $SiO_2$ supported Ni catalyst, the loading amount of active ingredient Ni is 18 wt %; firstly, hydrogen is fed in, then the catalyst material is heated up to 400° C. at a temperature increasing rate of 20° C. per hour and then goes through reduction reaction for 8 hours, and the temperature is subsequently reduced to 120° C.

Then, the equilibrium system containing the polyoxymethylene diethyl ethers products is refined by catalytic hydrogenation, and the process conditions are: the hydrogen pressure is 2 Mpa, the bed temperature of the fixed bed is 120° C., the space velocity of liquid is 0.5 $h^{-1}$, the hydrogen-to-oil ratio is 400:1, and the products are consecutively refined for 80 hours.

Finally, the formaldehyde contained is hydrogenated into methanol by the catalytic function of the $SiO_2$ supported Ni catalyst, and the methanol generated constitutes a component of the equilibrium products, thereby no other foreign component is generated while removing formaldehyde. The constituents and distribution of the main products before and after refining by catalytic hydrogenation are shown in Table 4-1.

TABLE 4-1 constituents and distribution of the main products before
and after refining by catalytic hydrogenation

| System | Constituents | | | | | | |
|---|---|---|---|---|---|---|---|
| | Ethanol wt % | Formaldehyde wt % | Methanol wt % | $PODE_1$ wt % | $\Sigma PODE_{2-6}$ wt % | Conversion rate of formaldehyde/% | Selectivity of catalyst/% |
| Before refining by hydrogenation | 5.1 | 4.7 | 0 | 38.0 | 52.2 | — | — |

TABLE 4-1-continued constituents and distribution of the main products before and after refining by catalytic hydrogenation

| System | Constituents | | | | | | |
|---|---|---|---|---|---|---|---|
| | Ethanol wt % | Formaldehyde wt % | Methanol wt % | $PODE_1$ wt % | $\Sigma PODE_{2-6}$ wt % | Conversion rate of formaldehyde/% | Selectivity of catalyst/% |
| After refining by hydrogenation | 5.1 | 0.00 | 4.7 | 38.0 | 52.2 | ~100 | ~100 |

Embodiment 5-2

This embodiment is based on the same synthesis product system as in Embodiment 5-1, but the refining step as in Embodiment 5-1 is omitted, instead the overall equilibrium system after synthesis directly enters the separation and purification unit, and Embodiment 5-1 and Embodiment 5-2 utilize the same separation and purification means to separate and purify the products with various polymerization degree.

The separation and purification process utilizes the atmospheric rectification technology, with tower plate number of 20~50, gas temperature of 45~65.0° C. at tower top, temperature of 110~130° C. at tower bottom, feedstock temperature of 60~90° C., and reflux ratio of 1.0~3.0. After the separation and purification is finished, the testing result of separation and purification efficiency of the products is shown in Table 4-2.

TABLE 4-2 separation and purification efficiency of the products

| Number | Constituents | | | |
|---|---|---|---|---|
| | Content of $\Sigma PODE_{2-6}$ in the equilibrium products/ wt % | Formaldehyde content after atmospheric rectification/ wt % | Recovery ratio of the target product $\Sigma PODE_{2-6}$/% | Purity of the target product $\Sigma PODE_{2-6}$/% |
| Embodiment 5-1 | 52.2 | 0.02 | ~100 | 99.8 |
| Embodiment 5-2 | 52.2 | 6.7 | <41.0 | ~93.3 |

Embodiment 6-1

Firstly, 20 ml supported Ni-based catalyst system is loaded into a fixed bed reactor of refining by hydrogenation, the supported Ni-based catalyst system is $ZrO_2$ supported Ni catalyst, the loading amount of active ingredient Ni is 18 wt %; firstly, hydrogen is fed in, then the catalyst material is heated up to 400° C. at a temperature increasing rate of 20° C. per hour and then goes through reduction reaction for 8 hours, and the temperature is subsequently reduced to 130° C.

Then, the equilibrium system containing the polyoxymethylene dipropyl ethers products is refined by catalytic hydrogenation, and the process conditions are: the hydrogen pressure is 5 Mpa, the bed temperature of the fixed bed is 130° C., the space velocity of liquid is 2 $h^{-1}$, the hydrogen-to-oil ratio is 300:1, and the products are consecutively refined for 80 hours.

Finally, the formaldehyde contained is hydrogenated into methanol by the catalytic function of the $ZrO_2$ supported Ni catalyst, and the methanol generated constitutes a component of the equilibrium products, thereby no other foreign component is generated while removing formaldehyde. The constituents and distribution of the main products before and after refining by catalytic hydrogenation are shown in Table 5-1.

The equilibrium system after refining by catalytic hydrogenation is separated and purified, and the separation and purification process utilizes the atmospheric rectification technology, with tower plate number of 20~50, gas temperature of 45~65.0° C. at tower top, temperature of 110~130° C. at tower bottom, feedstock temperature of 60~90° C., and reflux ratio of 1.0~3.0. After the separation and purification is finished, the testing result of separation and purification efficiency of the products is shown in Table 5-2. After the separation and purification is finished, the testing result of separation and purification efficiency of the products is shown in Table 5-2.

TABLE 5-1 constituents and distribution of the main products before and after refining by catalytic hydrogenation

| System | Constituents | | | | | | |
|---|---|---|---|---|---|---|---|
| | Propanol wt % | Formaldehyde wt % | Methanol wt % | $PODE_1$ wt % | $\Sigma PODE_{2-6}$ wt % | Conversion rate of formaldehyde/% | Selectivity of catalyst/% |
| Before refining by hydrogenation | 4.5 | 3.8 | 0 | 31.6 | 60.1 | — | — |
| After refining by hydrogenation | 4.5 | 0.00 | 3.8 | 31.6 | 60.1 | ~100 | ~100 |

Embodiment 6-2

This embodiment is based on the same synthesis product system (i.e. the equilibrium system) as in Embodiment 6-1, but the refining step as in Embodiment 6-1 is omitted, instead the overall equilibrium system after synthesis directly enters the separation and purification unit, and Embodiment 6-1 and Embodiment 6-2 utilize the same separation and purification means to separate and purify the products with various polymerization degree. After the separation and purification is finished, the testing result of separation and purification efficiency of the products is shown in Table 5-2.

TABLE 5-2 separation and purification efficiency of the products

| | Constituents | | | |
|---|---|---|---|---|
| Number | Content of $\Sigma PODE_{2-6}$ in the equilibrium products/ wt % | Formaldehyde content after atmospheric rectification/ wt % | Recovery ratio of the target product $\Sigma PODE_{2-6}$/% | Purity of the target product $\Sigma PODE_{2-6}$/% |
| Embodiment 6-1 | 60.1 | 0.01 | 99.8 | 99.9 |
| Embodiment 6-2 | 60.1 | 9.1 | ~47.0 | ~90.9 |

Then, the equilibrium system containing the polyoxymethylene dibutyl ethers products is refined by catalytic hydrogenation, and the process conditions are: the hydrogen pressure is 3 Mpa, the bed temperature of the fixed bed is 110° C., the space velocity of liquid is 2 $h^{-1}$, the hydrogen-to-oil ratio is 400:1, and the products are consecutively refined for 120 hours.

Finally, the formaldehyde contained is hydrogenated into methanol by the catalytic function of the Cu—Zn—Al catalyst, and the methanol generated constitutes a component of the equilibrium products, thereby no other foreign component is generated while removing formaldehyde. The constituents and distribution of the main products before and after refining by catalytic hydrogenation are shown in Table 6-1.

The equilibrium system after refining by catalytic hydrogenation is separated and purified, and the separation and purification process utilizes the atmospheric rectification technology, with tower plate number of 20~50, gas temperature of 45~65.0° C. at tower top, temperature of 110~130° C. at tower bottom, feedstock temperature of 60~90° C., and reflux ratio of 1.0~3.0. After the separation and purification is finished, the testing result of separation and purification efficiency of the products is shown in Table 6-2.

TABLE 6-1 constituents and distribution of the main products before and after refining by catalytic hydrogenation

| | Constituents | | | | | | |
|---|---|---|---|---|---|---|---|
| System | Butanol wt % | Formaldehyde wt % | Methanol wt % | $PODE_1$ wt % | $\Sigma PODE_{2-6}$ wt % | Conversion rate of formaldehyde/% | Selectivity of catalyst/% |
| Before refining by hydrogenation | 11.3 | 2.8 | 0 | 29.8 | 56.1 | — | — |
| After refining by hydrogenation | 11.3 | 0.00 | 2.8 | 29.8 | 56.1 | ~100 | ~100 |

Embodiment 7-1

Firstly, 20 ml unsupported Cu-based catalyst system is loaded into a fixed bed reactor of refining by hydrogenation, the unsupported Cu-based catalyst system is a Cu—Zn—Al catalyst, the content of active ingredient CuO is 60 wt %, the content of active ingredient ZnO is 20 wt %, and the content of $Al_2O_3$ is 20 wt %; firstly, hydrogen is fed in, then the catalyst material is heated up to 240° C. at a temperature increasing rate of 20° C. per hour and then goes through reduction reaction for 4 hours, and the temperature is subsequently reduced to 110° C.

Embodiment 7-2

This embodiment is based on the same synthesis product system as in Embodiment 7-1, but the refining step as in Embodiment 7-1 is omitted, instead the overall equilibrium system after synthesis directly enters the separation and purification unit, and Embodiment 7-1 and Embodiment 7-2 utilize the same separation and purification means to separate and purify the products with various polymerization degree. After the separation and purification is finished, the testing result of separation and purification efficiency of the products is shown in Table 6-2.

TABLE 6-2 separation and purification efficiency of the products

| Number | Content of $\Sigma PODE_{2-6}$ in the equilibrium products/ wt % | Formaldehyde content after atmospheric rectification/ wt % | Recovery ratio of the target product $\Sigma PODE_{2-6}$/% | Purity of the target product $\Sigma PODE_{2-6}$/% |
|---|---|---|---|---|
| Embodiment 7-1 | 56.1 | 0.02 | 99.5 | 99.8 |

TABLE 6-2-continued separation and purification efficiency of the products

| Number | Content of $\Sigma PODE_{2-6}$ in the equilibrium products/ wt % | Formaldehyde content after atmospheric rectification/ wt % | Recovery ratio of the target product $\Sigma PODE_{2-6}$/% | Purity of the target product $\Sigma PODE_{2-6}$/% |
|---|---|---|---|---|
| Embodiment 7-2 | 56.1 | 8.5 | ~47.0 | ~91.5 |

Embodiment 8-1

Firstly, unsupported Cu-based catalyst system is loaded into a fixed bed reactor of refining by hydrogenation, the unsupported Cu-based catalyst system is a Cu—Cr—Al catalyst, the content of active ingredient CuO is 52 wt %, the content of active ingredient $Cr_2O_3$ is 35 wt %, and the content of $Al_2O_3$ is 13 wt %; firstly, hydrogen is fed in, then the catalyst material is heated up to 220° C. at a temperature increasing rate of 20° C. per hour and then goes through reduction reaction for 6 hours, and the temperature is subsequently reduced to 130° C.

Then, the equilibrium system containing the polyoxymethylene dipentyl ethers products is refined by catalytic hydrogenation, and the process conditions are: the hydrogen pressure is 4 Mpa, the bed temperature of the fixed bed is 130° C., the space velocity of liquid is 1.5 h$^{-1}$, the hydrogen-to-oil ratio is 200:1, and the products are consecutively refined for 100 hours.

Finally, the formaldehyde contained is hydrogenated into methanol by the catalytic function of the Cu—Cr—Al catalyst, and the methanol generated constitutes a component of the equilibrium products, thereby no other foreign component is generated while removing formaldehyde. The constituents and distribution of the main products before and after refining by catalytic hydrogenation are shown in Table 7-1.

The equilibrium system after refining by catalytic hydrogenation is separated and purified, and the separation and purification process utilizes the atmospheric rectification technology, with tower plate number of 20~50, gas temperature of 45~65.0° C. at tower top, temperature of 110~130° C. at tower bottom, feedstock temperature of 60~90° C., and reflux ratio of 1.0~3.0. After the separation and purification is finished, the testing result of separation and purification efficiency of the products is shown in Table 7-2.

TABLE 7-1 constituents and distribution of the main products before and after refining by catalytic hydrogenation

| System | Pentanol wt % | Formaldehyde wt % | Methanol wt % | $PODE_1$ wt % | $\Sigma PODE_{2-6}$ wt % | Conversion rate of formaldehyde/% | Selectivity of catalyst/% |
|---|---|---|---|---|---|---|---|
| Before refining by hydrogenation | 8.4 | 4.1 | 0 | 37.2 | 50.3 | — | — |
| After refining by hydrogenation | 8.4 | 0.00 | 4.1 | 37.2 | 50.3 | ~100 | ~100 |

Embodiment 8-2

This embodiment is based on the same synthesis product system as in Embodiment 8-1, but the refining step as in Embodiment 8-1 is omitted, instead the overall equilibrium system after synthesis directly enters the separation and purification unit, and Embodiment 8-1 and Embodiment 8-2 utilize the same separation and purification means to separate and purify the products with various polymerization degree. After the separation and purification is finished, the testing result of separation and purification efficiency of the products is shown in Table 7-2.

TABLE 7-2 separation and purification efficiency of the products

| Number | Content of $\Sigma PODE_{2-6}$ in the equilibrium products/ wt % | Formaldehyde content after atmospheric rectification/ wt % | Recovery ratio of the target product $\Sigma PODE_{2-6}$/% | Purity of the target product $\Sigma PODE_{2-6}$/% |
|---|---|---|---|---|
| Embodiment 8-1 | 50.3 | 0.02 | 99.5 | 99.8 |
| Embodiment 8-2 | 50.3 | 6.7 | ~43.0 | ~93.3 |

It can be seen from the data of separation and purification in the foregoing embodiments that, in the equilibrium system obtained by the synthesis unit, if the formaldehyde contained is not specifically removed, then no matter how ideal the product distribution of the synthesis part is, it is always unable to obtain satisfactory products. However, the system that has been through the refining process by hydrogenation of the present invention only requires simple ordinary separation and purification operations to achieve separation and purification of products with various polymerization degree and to obtain the effects of satisfactory product yield and product purity. Therefore, as a step of the entire production process, the refining unit plays a crucial role in obtaining of the target products. More importantly, the technological process of the present invention for refining by catalytic hydrogenation using a fixed bed achieves an atom utilization ratio close to 100%, does not discharge any waste water or waste residue during the entire process, not only has satisfactory separation and purification results, but also is green and environmental as a whole, which has great practical significance.

Obviously, the aforementioned embodiments are merely intended for clearly describing the examples, rather than limiting the implementation scope of the invention. For those skilled in the art, various changes and modifications in other different forms can be made on the basis of the aforementioned description. It is unnecessary and impossible to exhaustively list all the implementation ways herein. However, any obvious changes or modifications derived from the aforementioned description are intended to be embraced within the protection scope of the present invention.

The invention claimed is:

1. A method for refining polyoxymethylene dialkyl ethers by catalytic hydrogenation using a fixed bed, comprising:
performing catalytic hydrogenation using a fixed bed reactor and in the presence of catalyst, of an equilibrium system containing polyoxymethylene dialkyl ether products and formaldehyde to produce refined polyoxymethylene dialkyl ether products having formaldehyde contained therein removed, and
performing separation and purification operations on the refined products after formaldehyde removal.

2. The method for refining polyoxymethylene dialkyl ethers by catalytic hydrogenation using a fixed bed in accordance with claim 1, wherein said catalyst is a supported Ni-based catalyst system, or an unsupported Cu-based catalyst system.

3. The method for refining polyoxymethylene dialkyl ethers by catalytic hydrogenation using a fixed bed in accordance with claim 2, wherein said supported Ni-based catalyst system is a Ni/$Al_2O_3$ supported catalyst modified by K, Mg or Zn, wherein, calculated on the total mass of the catalyst, the loading amount of active ingredient Ni is 5-25 wt %, and the loading amount of said K, Mg or Zn is 0.5-5 wt %.

4. The method for refining polyoxymethylene dialkyl ethers by catalytic hydrogenation using a fixed bed in accordance with claim 3, wherein in said supported Ni-based catalyst system, the loading amount of said active ingredient Ni is 10-20 wt %, and the loading amount of said K, Mg or Zn is 1-3 wt %.

5. The method for refining polyoxymethylene dialkyl ethers by catalytic hydrogenation using a fixed bed in accordance with claim 2, wherein said supported Ni-based catalyst system is $ZrO_2$, $SiO_2$ or activated carbon supported Ni catalyst, wherein, calculated on the total mass of the catalyst, the loading amount of active ingredient Ni is 15-20 wt %.

6. The method for refining polyoxymethylene dialkyl ethers by catalytic hydrogenation using a fixed bed in accordance with claim 5, wherein in said supported Ni-based catalyst system, the loading amount of said active ingredient Ni is 18-20 wt %.

7. The method for refining polyoxymethylene dialkyl ethers by catalytic hydrogenation using a fixed bed in accordance with claim 2, wherein said unsupported Cu-based catalyst system is an unsupported Cu—Zn—Al catalyst, wherein, calculated on the total mass of the catalyst, the content of active ingredient CuO is 25-60 wt %, the content of active ingredient ZnO is 20-50 wt %, and the content of $Al_2O_3$ is 5-25 wt %.

8. The method for refining polyoxymethylene dialkyl ethers by catalytic hydrogenation using a fixed bed in accordance with claim 2, wherein said unsupported Cu-based catalyst system is an unsupported Cu—Cr—Al catalyst, wherein, calculated on the total mass of the catalyst, the content of active ingredient CuO is 30-60 wt %, the content of active ingredient $Cr_2O_3$ is 10-45 wt %, and the content of $Al_2O_3$ is 10-30 wt %.

9. The method for refining polyoxymethylene dialkyl ethers by catalytic hydrogenation using a fixed bed in accordance with claim 1, wherein the amount of formaldehyde contained in said equilibrium system containing polyoxymethylene dialkyl ether products is 0.5-20 wt %.

10. The method for refining polyoxymethylene dialkyl ethers by catalytic hydrogenation using a fixed bed in accordance with claim 1, wherein said catalytic hydrogenation is carried out at a hydrogen pressure of 1-10 Mpa, a reaction temperature of 80-160° C., a liquid space velocity of 0.5-4 $h^{-1}$, and a hydrogen-to-oil volume ratio of 100:1-600:1.

11. The method for refining polyoxymethylene dialkyl ethers by catalytic hydrogenation using a fixed bed in accordance with claim 2, wherein said catalytic hydrogenation is carried out at a hydrogen pressure of 1-10 Mpa, a reaction temperature of 80-160° C., a liquid space velocity of 0.5-4 $h^{-1}$, and a hydrogen-to-oil volume ratio of 100:1-600:1.

12. The method for refining polyoxymethylene dialkyl ethers by catalytic hydrogenation using a fixed bed in accordance with claim 10, wherein said catalytic hydrogenation is carried out at a hydrogen pressure of 2-6 Mpa, a reaction temperature of 100-130° C., a liquid space velocity of 1-2 $h^{-1}$, and a hydrogen-to-oil volume ratio of 200:1-400:1.

13. The method for refining polyoxymethylene dialkyl ethers by catalytic hydrogenation using a fixed bed in accordance with claim 11, wherein said catalytic hydrogenation is carried out at a hydrogen pressure of 2-6 Mpa, a reaction temperature of 100-130° C., a liquid space velocity of 1-2 $h^{-1}$, and a hydrogen-to-oil volume ratio of 200:1-400:1.

14. The method for refining polyoxymethylene dialkyl ethers by catalytic hydrogenation using a fixed bed in accordance with claim 1, wherein said separation and purification operations comprise one or more operations selected from the group consisting of atmospheric distillation, vacuum distillation, flash evaporation, rectification, phase separation and filtration.

* * * * *